US009314528B2

(12) United States Patent
Vehige et al.

(10) Patent No.: US 9,314,528 B2
(45) Date of Patent: *Apr. 19, 2016

(54) EFFICIENT LIPID DELIVERY TO HUMAN TEAR FILM USING A SALT-SENSITIVE EMULSION SYSTEM

(71) Applicant: Allergan, Inc., Irvine, CA (US)

(72) Inventors: Joseph G. Vehige, Laguna Niguel, CA (US); Peter A. Simmons, Yorba Linda, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/708,771

(22) Filed: Dec. 7, 2012

(65) Prior Publication Data

US 2013/0197083 A1 Aug. 1, 2013

Related U.S. Application Data

(60) Provisional application No. 61/568,089, filed on Dec. 7, 2011, provisional application No. 61/625,401, filed on Apr. 17, 2012.

(51) Int. Cl.
*A61K 31/047* (2006.01)
*A61K 47/32* (2006.01)
*A61K 31/341* (2006.01)
*A61K 31/717* (2006.01)
*A61K 9/00* (2006.01)
*A61K 9/107* (2006.01)

(52) U.S. Cl.
CPC .............. *A61K 47/32* (2013.01); *A61K 9/0048* (2013.01); *A61K 9/107* (2013.01); *A61K 31/047* (2013.01); *A61K 31/341* (2013.01); *A61K 31/717* (2013.01)

(58) Field of Classification Search
CPC .. A61K 31/047; A61K 31/341; A61K 31/717
See application file for complete search history.

(56) References Cited

U.S. PATENT DOCUMENTS

| 4,201,706 A | 5/1980 | Trager et al. |
| 5,145,871 A | 9/1992 | Cavazza |
| 5,192,535 A | 3/1993 | Davis et al. |
| 5,432,199 A | 7/1995 | Cavazza |
| 5,527,831 A | 6/1996 | Franz et al. |
| 5,827,512 A | 10/1998 | Gleich |
| 6,156,293 A | 12/2000 | Jutila et al. |
| 6,193,957 B1 | 2/2001 | Ahmed |
| 6,228,392 B1 | 5/2001 | Morcos et al. |
| 6,365,622 B1 | 4/2002 | Cavazza |
| 6,555,526 B2 | 4/2003 | Matsuo et al. |
| 6,585,987 B1 | 7/2003 | Fransoni |
| 7,045,121 B2 | 5/2006 | Chang et al. |
| 8,569,367 B2 | 10/2013 | Vehige et al. |
| 2002/0071874 A1 | 6/2002 | Olejnik et al. |
| 2004/0137079 A1 | 7/2004 | Cook et al. |
| 2004/0192647 A1 | 9/2004 | Babizhayev |
| 2005/0009836 A1 | 1/2005 | Laskar et al. |
| 2006/0035842 A1 | 2/2006 | Tsuzuki et al. |
| 2008/0026991 A1* | 1/2008 | Rabinovich-Guilatti et al. ............... 514/11 |

FOREIGN PATENT DOCUMENTS

| EP | 0028110 A2 | 5/1981 |
| EP | 0436726 | 7/1990 |
| EP | 0778021 | 6/1997 |
| JP | 2763400 | 3/1998 |
| JP | 2010-036255 | 2/2010 |
| WO | 98-41208 | 9/1998 |
| WO | 02-38161 | 5/2002 |
| WO | 03-051332 | 6/2003 |
| WO | 2004-084877 | 7/2004 |
| WO | 2008-106228 A2 | 9/2008 |
| WO | 2010-141648 | 12/2010 |

OTHER PUBLICATIONS

Patent Cooperation Treaty, International Search Report and Written Opinion, Feb. 22, 2013, International Application No. PCT/US2012/068603.
Patent Cooperation Treaty, International Search Report and Written Opinion, Feb. 22, 2013, International Application No. PCT/US2012/068615.
Albietz, Julie et al, A Comparison of the Effect of Refresh plus and Bion Tears on Dry Eye Symptoms and Ocular Surface Health in Myopic LASIK Patients, the CLAO Journal, 2002, 96-100, 28(2).
Alfieri, Roberta et al, Compatible Osmolytes Modulate the Response of Porcine Endothelial Cells to Hypertonicity and Protect Them From Apoptosis, J. Physiol., 2002, 499-508, 540.
Barker, Robert et al, Acidic Polyamino Acids Inhibit Human Eosinophil Granule Major Basic Protein Toxicity. Evidence of a Functional Role for ProMBP, J. Clin. Invest., Sep. 1991, 798-805, 88.
Biocompare®: Product Review: Upstate's Beadlyte Human/Mouse Cytokine Detection Kits, Jun. 15, 2004, 3 Pages, Biocompare, Inc.
Brown, Theodore et al, Glossary: Salt, Chemistry: The Central Science, 2006, G-10, 10th Edition.
Burg, Maurice, Molecular Basis of Osmotic Regulation, American Physiological Society, 1995, F983-F996, 268.
Cammarata, Patrick et al, Osmoregulatory Alterations in taurine Uptake by Cultured Human and Bovine lens Epithelial Cells, Invest. Ophthalmol. Vis. Sci., 2002, 425-433, 43.
Gilbard, Jeffrey, Tear Film Osmolarity and Keratoconjunctivitis Sicca, the CLAO Journal, Jul. 1985, 243-250, 11 (3).
Matsuo, Toshihiko et al, Trehalose Eye Drops in the Treatment of Dry Eye Syndrome, Ophthalmology, 2002, 2024-2029, 109.
McGrogan, Michael et al, Isolation of a Complementary DNA Clone Encoding a Precursor to Human Eosinophil Major Basic Protein, J. Exp. Med., Dec. 1988, 2295-2308, 168.
Nakajima, Toshiharu et al, Gene Expression Screening of Human Mast Cells and Eosinophils Using High-Density Oligonucleotide Probe Arrays: Abundant Expression of Major Basic Protein in Mast Cells, Blood, Aug. 2001, 1127-1134, 98 (4).

(Continued)

*Primary Examiner* — Zohreh Fay
(74) *Attorney, Agent, or Firm* — Lorenz Siddiqi

(57) ABSTRACT

Provided herein are low salt ophthalmic pharmaceutical composition and methods of use thereof, for example, in the treatment of dry eye syndrome.

18 Claims, 7 Drawing Sheets

(56) References Cited

OTHER PUBLICATIONS

Peluso, Gianfranco et al, Carnitine: An Osmolyte That Plays a Metabolic Role, Journal of Cellular Biochemistry, 2000, 1-10, 80.

Pessotto, P. et al, The Presence of L-Carnitine in Ocular Tissues of the Rabbit, Journal of Ocular Pharmacology, 1994, 643-651, 10 (4).

Popken-Harris, Pamela et al, Biochemical Properties, Activities, and Presence in Biologic Fluids of Eosinophil Granule Major Basic Protein, J. Allergy Clin. Immunol., 1994, 1282-1289, 94 (6).

Popken-Harris, Pamela et al, Regulation and Processing of a Precursor Form of Eosinophil Granule Major Basic Protein (ProMBP) in Differentiating Eosinophils, Blood, Jul. 1998, 623-631, 92 (2).

Rhyne, P.W. et al, Analysis of Apoptotic Cells Using Beadlyte Suspension Arrays, Biotechniques, Sep. 2003, 624-629 (Abstract), 35 (3).

Shioda, Ryo et al, Osmosensitive Taurine Transporter Expression and Activity in Human Corneal Epithelial Cells, Investigative Ophthalmology & Visual Science, Sep. 2002, 2916-2922, 43 (9).

Voet et al, Transport Across the Mitochondrial Membrane, Biochemistry, 1990, 622.

* cited by examiner

EFFICIENT LIPID DELIVERY TO HUMAN TEAR FILM USING A SALT-SENSITIVE EMULSION SYSTEM

CROSS-REFERENCES TO RELATED APPLICATIONS

This application claims the benefit of U.S. Provisional Application Ser. Nos. 61/568,089, filed Dec. 7, 2011 and 61/625,401 filed Apr. 17, 2012, the disclosures of which are hereby incorporated in their entirety herein by reference.

BACKGROUND OF THE INVENTION

The present application relates to compositions and methods to supplement and enhance the native tear film of the eye, e.g., the native lipid layer of the tear film. The compositions and methods disclosed herein provide inter alia relief of hyperosmotic stress and other conditions associated with dry eye syndrome.

Delivering therapeutic agents, e.g., therapeutic lipids, to supplement and enhance the native tear film is a recognized strategy in treating symptoms of dry eye syndrome. Without wishing to be bound by any theory, it is believed that this strategy is especially advantageous under conditions of low humidity or when other factors increase tear film evaporation. In dry eye syndrome, loss of water in the tear film can lead to increased salt content at the ocular surface, which in turn can lead to hyperosmotic stress to the cells of the ocular surface. It is further believed that the native lipid layer of the tear film functions inter alia to reduce evaporation from the underlying aqueous tear film layer. Accordingly, in cases where the native lipid layer is reduced, e.g., in disorders or conditions described herein or known in the art, it is believed that supplementation and enhancement of the lipid layer of the tear film is beneficial.

The lipid layer of the native tear film is quite thin (i.e., 0.1-0.2 micron). Moreover, the total volume of lipid in the tear film is but a small fraction of the total tear film volume. Thus, previous methods of supplementation and enhancement of the structure and function of the lipid layer of the tear film by topical application of a lipid-containing pharmaceutical composition require merely a small therapeutically effective volume of lipid to be delivered. In such methods, however, excess lipid provided during instillation can displace and disrupt the aqueous component of the tear film. Because the lipid delivered by such methods needs to become established as part of the native lipid layer, at the air interface over the aqueous tear, methods which reduce the aqueous layer of the tear film can afford reduced effectiveness. Moreover, any topical drop delivery method of supplementation and enhancement of the lipid layer of the tear film requires rapid delivery during the brief contact time of the topical eye drop with the ocular surface.

Thus, previous methods of supplementing and enhancing the lipid layer of the tear film have been addressed by a variety of approaches, including using a substantial amount of lipid (e.g., 1-5%) and/or building an emulsion system that readily separates. However, such methods suffer multiple disadvantages, including a requirement for shaking of the composition prior to instillation, reduced clarity of the composition upon instillation, variability of the total volume of lipid delivered to the eye, and problems with tolerability vis-a-vis aqueous eye drops.

The present invention provides, inter alia, compositions and methods directed to an alternate means of lipid release by the use of a salt-sensitive emulsion system in a ophthalmic pharmaceutical composition which is largely free of salt. Specifically, the present compositions employ a surfactant and a salt-sensitive viscosity modulating polymer to hold a therapeutic lipid (e.g., castor oil) in a stable sub-micron emulsion. When instilled in the eye, the composition mixes with the native tear film, the natural salt content of which is sufficient to cause a rapid decrease in viscosity due to changes in the salt-sensitive viscosity modulating polymer. Upon loss of viscosity, therapeutic lipid is released from the sub-micron emulsion at the eye, thereby providing supplementation and enhancement of the native lipid layer of the tear film.

BRIEF SUMMARY OF THE INVENTION

In a first aspect, there is provided a low salt ophthalmic pharmaceutical composition which includes a sub-micron emulsion, a polymer lubricant, and a salt-sensitive viscosity modulating polymer, wherein the sub-micron emulsion includes a surfactant and a therapeutic lipid.

In another aspect, there is provided a low salt ophthalmic pharmaceutical composition including: castor oil at a concentration of about 0.25% (w/w); polysorbate 80 at a concentration of about 0.5% (w/w); acrylate/$C_{10}$-$C_{30}$ acrylate crosspolymer at a concentration of about 0.1% (w/w), wherein said acrylate/$C_{10}$-$C_{30}$ acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.

In another aspect, there is provided a method for treating dry eye syndrome. The method includes administering to a subject in need of treatment of dry eye syndrome a low salt ophthalmic pharmaceutical composition as described herein, thereby treating the dry eye syndrome.

BRIEF DESCRIPTION OF THE DRAWINGS

FIG 1.

FIG 2.

FIG 3.

FIG 4.

DETAILED DESCRIPTION OF THE INVENTION

I. Definitions

Figure 1A:
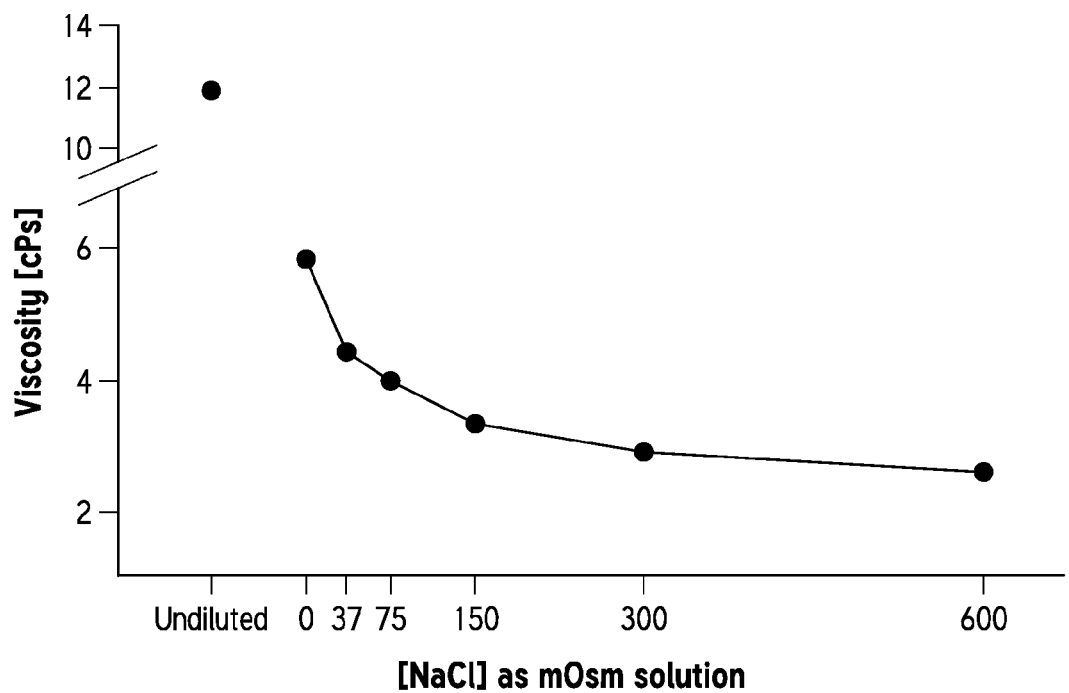
FIG. 1A depicts the dependence of viscosity (cPs) on salt concentration for a low salt ophthalmic pharmaceutical composition disclosed herein. See Example 1.

Unless indicated otherwise, the term "tear" as used herein refers in the customary sense to the basal tears of the mammalian eye which function to continuously bathe and nourish the cornea. Other types of tear include reflex tears resulting e.g., from irritation of the eye by foreign particles or lacrimator compounds, and psychic tears resulting, e.g., from strong emotional stress, anguish, or physical pain.

The terms "tear film," "precorneal film" and like refer in the customary sense to the multilayered coating of the normal eye which includes an innermost mucous layer, a middle aqueous layer, and an outermost lipid layer. The innermost mucous layer contains proteins, e.g., mucin produced by the goblet cells of the conjunctiva, and facilitates even spreading of the overlying middle aqueous layer, e.g., by providing a hydrophilic layer coating the cornea. The middle aqueous layer is produced by the lacrimal glands and includes water, proteins and salt as known in the art. The outermost lipid layer contains oils produced by the meibomian glands and coats the middle aqueous layer, providing a hydrophobic barrier that envelopes tears and prevents outflow, e.g., to the cheek. Importantly, the outermost lipid layer decreases evaporation of the middle aqueous layer.

The terms "dry eye," "dry eye syndrome," "keratitis sicca," "xerophthalmia," "keratoconjunctivits sicca," and the like refer in the customary sense to a condition or spectrum of conditions wherein the eye is unable to maintain a healthy tear layer (i.e., tear film) sufficient to coat the eye. Dry eye syndrome is more prevalent with age, as subjects typically produce fewer tears with age.

The term "about" in the context of a numerical value refers, absent express indication otherwise, to the nominal amount ±10% thereof.

The term "low salt" as used herein in the context of a ophthalmic pharmaceutical composition refers to a salt content which is sufficiently low so as to provide a stabilized sub-micron emulsion within the ophthalmic pharmaceutical composition. Salt content can be measured by a variety of methods known in the art, e.g., measurement of ionic strength. Accordingly, the term "low salt ophthalmic pharmaceutical composition" refers to a pharmaceutical composition for use in the eye having sufficiently low salt content that a sub-micro emulsion which includes a surfactant and a therapeutic lipid is stable therein.

The term "sub-micron emulsion" refers to an emulsion containing components having an extent in the longest dimension of less than about 1 micron. "Emulsion" refers in the customary sense to a mixture of two or more immiscible liquid components, one component (e.g., a therapeutic lipid described herein or mixture thereof including surfactant) being dispersed through the other component (e.g., the aqueous component of a composition described herein).

The term "polymer lubricant" refers to a polymeric agent able coat the ocular surface (i.e., demulcent) and provide lubrication to the eye. Exemplary polymer lubricants useful in the composition and methods disclosed herein include any of a variety of cellulose derivatives, e.g., hydroxymethyl cellulose, hydroxyethyl cellulose, carboxymethyl cellulose and the like, polyvinyl pyrrolidone, polyvinyl alcohol, and the like, and mixtures thereof.

The terms "salt-sensitive viscosity modulating polymer," "salt-sensitive polymer" and the like refer to polymeric agents useful to maintain a stable sub-micron emulsion under low salt conditions within a low salt ophthalmic pharmaceutical composition disclosed herein, and which in turn destabilize, upon an increase in salt content, the sub-micron emulsion. The term "destabilize" in this context refers to a change in the sub-micron emulsion such that therapeutic lipid is released from the sub-micron emulsion. Accordingly, the terms "salt-sensitive" and the like in this context refer to a change in one or more properties of a compound (e.g., conformation, extent of hydration, effective charge due to ion screening, viscosity and the like) in response to a change in salt concentration. Exemplary salt-sensitive viscosity modulating polymers include polymers of acrylic acid which are crosslinked with polyalkenyl ethers or divinyl glycol. A preferred salt-sensitive viscosity modulating polymer includes crosslinked copolymers of acrylic acid and $C_{10}$-$C_{30}$ alkyl acrylate, commonly referred to as Pemulen™ TR-2 (Lubrizol Corporation, Wickliffe, Ohio).

The term "surfactant" refers in the customary sense to compounds able to lower the surface tension of liquid, the interfacial tension between two liquids, or the surface tension between a liquid and a solid.

The term "therapeutic lipid" refers to a pharmaceutically acceptable amphiphilic or hydrophobic agent which acts to supplement and/or enhance the naturally occurring oils produced by the meibomian glands which form the outermost lipid layer of the tear film. In some embodiments, the therapeutic lipid is a hydrophobic agent. Without wishing to be bound by any theory, it is believed that symptoms of dry eye syndrome can result from insufficient production of naturally occurring oils produced by the meibomian glands. Accordingly, it is further believed that supplement and/or enhancement by a therapeutic lipid described herein is beneficial to the treatment of dry eye syndrome.

The terms "clear," "clarity" and the like in the context of ophthalmic pharmaceutical compositions refer to absorbance and/or light scattering (e.g., opacity, pearlesence, and the like) which are sufficiently low such that the ophthalmic pharmaceutical composition appears substantially free of haziness, mistiness or cloudiness to the naked human eye. A clear ophthalmic pharmaceutical composition does not include emulsions that visibly separate into a hydrophobic portion and a hydrophilic portion.

The terms "compatible solute," "osmolytes" and the like in the context of ophthalmic pharmaceutical compositions refers to substances that are taken into the cell and act to counterbalance the osmotic pressure found outside the cell. Without wishing to be bound by any theory, it is believed that compatible solutes have osmoprotective properties which may protect the surface cells of the eye from osmotic stress. It is further believed that the incorporation of compatible solutes increases the clinical usefulness of the composition disclosed herein to contemplate a broader range of subject suffering from dry eye syndrome compared to previous emulsion systems which target lipid deficiency per se or meibomian gland dysfunction.

The term "tonicity agent" as used herein refers in the customary sense to a compound which can modulate the effective osmotic pressure within a cell. For example, for comfort during administration or instillation, the tonicity of pharmaceutical dosage forms can be adjusted by a tonicity agent. Exemplary tonicity agents include dextrose, glycerin, mannitol, KCl, and NaCl. Tonicity agents can provide additional benefit, including e.g., function as a humectant or lubricant.

The term "sorbitan ester" in the context of surfactants refers in the customary sense to a class of polyethylene glycol (i.e., PEG) derivatives of sorbitan which are further esterified with fatty acids, as known in the art.

The term "standard emulsion viscosity" as used herein refers to the experimentally determined viscosity of a 0.2% solution of salt-sensitive viscosity modulating polymer as measured in a standardized procedure according to manufacturer's recommendation. See e.g., Lubrizol Test Procedure SA-015, Ed: August, 2003, Lubrizol Advanced Materials, Inc., Cleveland, Ohio.

The term "treatment" as used herein refers to an approach (e.g., a procedure or regimen) for obtaining beneficial or desired results, including clinical results. "Treating," "palliating," or "ameliorating" a disease, disorder or condition means that the extent, undesirable clinical manifestations, or both, of a disease, disorder or condition are lessened and/or the time course of the progression is slowed (i.e., lengthened in time), as compared to not treating the disease, disorder or condition. For purposes of the methods disclosed herein, beneficial or desired clinical results include, but are not limited to, alleviation or amelioration of one or more symptoms (e.g., symptoms of dry eye syndrome), diminishment of extent of disorder, stabilized (i.e., not worsening) state of disorder, delay or slowing of disorder progression, amelioration or palliation of the disorder, and remission (whether partial or total), whether detectable or undetectable.

The terms "effective amount," "therapeutically effective amount" and the like in the context of compositions and methods disclosed herein refer in the customary sense to an amount which is sufficient to bring about a desired result. Accordingly, a therapeutically effective amount employed in a treatment is a sufficient amount to reduce the extent, undesirable clinical manifestation, of both, of a disease, disorder or condition.

II. Design Rationale

The salt-sensitive viscosity modulating polymers contemplated in the practice of the compositions and methods disclosed herein undergo a salt-sensitive change in physical properties (e.g., change in viscosity) upon a change in salt concentration in the milieu of a sub-micron emulsion containing the polymers. Specifically, upon an increase in salt concentration, the sub-micron emulsions undergo a decrease in viscosity. Without wishing to be bound by any theory, it is believed that such a decrease in viscosity is associated with a destabilization of the sub-micron emulsion leading to separation of the lipid phase (e.g., therapeutic lipid) from associated surfactant, which therapeutic lipid then becomes available to exert a therapeutic benefit in the supplementation and enhancement of the outer lipid layer of the tear film.

Traditionally, ionic or non-ionic surfactants stabilize oil-in-water emulsions by the formation of lamallar liquid crystalline layers at the emulsion interface to afford micelles, as known in the art. However, as further known in the art, such traditional methods of emulsification require relatively high levels (e.g., 3-7%) of surfactant. Without wishing to be bound by any theory, it is believed that the salt-sensitive viscosity modulating polymers contemplated herein increase the stability of oil-in-water emulsions under low salt conditions by thickening and adding structure to the water phase, resulting in an aqueous gel around each oil droplet. Thus, incorporation of salt-sensitive viscosity modulating polymers reduces the requirement for relatively high levels of surfactant in order to achieve stable emulsification. It is further believed that the hydrophobic portions of the salt-sensitive viscosity modulating polymers associate with the oil droplet. Thus, when two emulsified oil droplets approach each other, a physical repulsive force is generated by the presence of the adsorbed gel layers. Accordingly, the oil droplets do not associate with each other and remain in a stable sub-micron emulsion. Moreover, by decreasing the total therapeutic lipid content of the composition, it is believed that the compositions disclosed herein provide improved tolerability in the clinic.

As known in the art, tears (i.e., basal tears) have about the same osmolality as the internal fluids of the body, equivalent to about 0.9% NaCl (i.e., about 150 mM). Moreover, without wishing to be bound by any theory, it is believed that in dry eye syndrome, the middle aqueous layer of the tear film can undergo evaporation leading to increased local salt concentration at the eye. Thus, it has been found that application of a composition disclosed herein to the eye can result in destabilization of the sub-micron emulsion of the composition due to the increased salt content at the eye, thereby providing therapeutic lipid beneficial at the surface of the eye. Moreover, without wishing to be bound by any theory, it is believed that higher salt content of the nascent tear film and underlying corneal surface found in dry eye syndrome can result in greater delivery of therapeutic lipid, due to more effective destabilization of the sub-micron emulsion and release of therapeutic lipid.

Moreover, it has been surprisingly found that a further benefit of the compositions disclosed herein is a lack of coalescence of the therapeutic lipid upon instillation in the eye, resulting in no increase in lipid droplet size. Accordingly, the lipid can mix more effectively into the native tear film.

III. Compositions

In a first aspect, there is provided a low salt ophthalmic pharmaceutical composition which includes a sub-micron emulsion, a polymer lubricant, and a salt-sensitive viscosity modulating polymer. The sub-micron emulsion includes a surfactant and a therapeutic lipid.

In one embodiment, the low salt ophthalmic pharmaceutical composition is clear. In one embodiment, the composition has approximately the same clarity as pure water (e.g. upon inspection with the naked human eye). Thus, in some embodiments, the composition scatters sufficiently low levels of visible light that the composition appears clear to the eye. In one embodiment, the composition is effectively clear. The term "effectively clear" refers to a small amount of absorbance and/or light scattering which nonetheless allows light to transit the composition without appreciable blurring and/or distortion. In some embodiments, the clear low salt ophthalmic pharmaceutical composition allows transmission of at least about 20% T of visible light. In some embodiments, the clear low salt ophthalmic pharmaceutical composition allows transmission of at least about 25% T of visible light. In some embodiments, the clear low salt ophthalmic pharmaceutical composition allows transmission of at least about 30% T of visible light. In some embodiments, the clear low salt ophthalmic pharmaceutical composition allows transmission of at least about 35% T of visible light. In some embodiments, the clear low salt ophthalmic pharmaceutical composition allows transmission of at least about 40% T of visible light. In some embodiments, the clear low salt ophthalmic pharmaceutical composition allows transmission of at least about 45% T of visible light. In some embodiments, the clear low salt ophthalmic pharmaceutical composition allows transmission of at least about 50% T of visible light. In some embodiments, the clear low salt ophthalmic pharmaceutical composition allows transmission of at least about 55% T of visible light. In some embodiments, the clear low salt ophthalmic pharmaceutical composition allows transmission of at least 60% T of visible light. In some embodiments, the clear low salt ophthalmic pharmaceutical composition allows transmission of at least 65% T of visible light. In some embodiments, the clear low salt ophthalmic pharmaceutical composition allows transmission of at least 70% T of visible light. In some embodiments, the clear low salt ophthalmic pharmaceutical composition allows transmission of at least 75% T of visible light. In some embodiments, the clear low salt ophthalmic pharmaceutical composition allows transmission of at least 80% T of visible light. Absent an indication otherwise, "% T" refers to percentage transmission of light using a path length of 1 cm.

Further to any embodiment disclosed herein, in one embodiment the therapeutic lipid is a fatty acid glyceride. In one embodiment, the fatty acid glyceride is a castor oil, olive oil, peanut oil, corn oil, or sunflower oil.

In one embodiment, the therapeutic lipid is castor oil. In one embodiments, the castor oil is present at a concentration between about 0.01% (w/w) and about 10% (w/w). In one embodiment, the castor oil is present at a concentration of about 0.25% (w/w).

In one embodiment, the composition includes a plurality of therapeutic lipids. For example, in one embodiment the therapeutic lipid is a first therapeutic lipid, and the low salt ophthalmic pharmaceutical composition further includes a second therapeutic lipid. In one embodiment, the composition further includes a third therapeutic lipid. In one embodiment, the composition further includes a fourth therapeutic lipid. In one embodiment, the composition further includes a fifth therapeutic lipid. Further to each embodiment contemplating a plurality of therapeutic lipids, the first, second, third, fourth and fifth therapeutic lipids are each different and if present are castor oil, olive oil, peanut oil, corn oil, or sunflower oil.

Further to any embodiment including a plurality of therapeutic lipids, in one embodiment the plurality of therapeutic lipids are present at a total concentration between about 0.01% (w/w) and about 10% (w/w). In one embodiment, the plurality of therapeutics lipids are present at a concentration of about 0.25% (w/w).

In one embodiment, the surfactant within the low salt ophthalmic pharmaceutical composition is a sorbitan ester. Exemplary surfactants contemplated for use in the compositions and methods disclosed herein include polysorbate 20 (i.e., primarily polyoxyethylene [20] sorbitan monolaurate), polysorbate 40 (i.e., primarily polyoxyethylene [20] sorbitan monopalmitate), polysorbate 60 (i.e., primarily polyoxyethylene [20] sorbitan monostearate), or polysorbate 80 (i.e., polyoxyethylene [20] sorbitan monooleate).

In one embodiment, the surfactant is polysorbate 80. In one embodiment, polysorbate 80 is present at a concentration between about 0.01% (w/w) and about 1.0% (w/w). In one embodiment, polysorbate 80 is present at a concentration of about 0.5% (w/w).

In one embodiment, the salt-sensitive viscosity modulating polymer of the low salt ophthalmic pharmaceutical composition is an acrylate/$C_{10}$-$C_{30}$ acrylate crosspolymer. In one embodiment, the salt-sensitive viscosity modulating polymer has a standard emulsion viscosity between 1,700 and 4,500 cPs. A useful commercially available acrylate/$C_{10}$-$C_{30}$ acrylate crosspolymer is known as Pemulen™ TR-2 (Lubrizol Corporation, Wickliffe, Ohio).

In one embodiment, the salt-sensitive viscosity modulating polymer of the low salt ophthalmic pharmaceutical composition is present at a concentration between about 0.01% (w/w) and about 1.0% (w/w). In one embodiment, the salt-sensitive viscosity modulating polymer is present at a concentration of about 0.1% (w/w).

Further to any embodiment described above, in one embodiment of the low salt ophthalmic pharmaceutical composition is a demulcent.

Further to any embodiment described above, in one embodiment the polymer lubricant is a carboxymethylcellulose lubricant. As customarily used in the art, the terms "carboxymethylcellulose," "cellulose gum," "CMC" and the like refer to cellulose derivatives having carboxymethyl (i.e., —$CH_2$—COOH) groups substituted at some of the pendant hydroxyl moieties of the polymerized D-glucose units forming the linear chain of the cellulose. Cellulose chain length and the degree of carboxymethylation can be optimized to afford specific properties, including viscosity modulation (i.e., thickening) and stabilization of emulsions. Accordingly, the term "carboxymethylcellulose lubricant" refers to a composition including one or more carboxymethylcelluloses having specific chain lengths and degrees of carboxymethylation.

In one embodiment, the polymer lubricant is carboxymethylcellulose sodium, preferably carboxymethylcellulose sodium (low viscosity, 7LFPH). In one embodiment, the carboxymethylcellulose sodium is present at a concentration between about 0.01% (w/w) and about 1.0% (w/w). In one embodiment, the carboxymethylcellulose sodium is present at a concentration of about 0.5% (w/w).

Further to any embodiment described above, in one embodiment the low salt ophthalmic pharmaceutical composition further includes one or more compatible solutes. Exemplary compatible solutes includes polyols and zwitterionic amino acids. In one embodiment, the compatible solute is a polyol. In one embodiment, the compatible solute is a zwitterionic amino acid. In one embodiment, the compatible solute includes polyols and zwitterionic amino acids. In one embodiment, the compatible solute includes a polyol and a zwitterionic amino acid.

In one embodiment, the low salt ophthalmic pharmaceutical composition includes erythritol or levocarnitine. In one embodiment, erythritol is present at a concentration between about 0.01% (w/w) and about 1.0% (w/w). In one embodiment, levocarnitine is present at a concentration between about 0.01% (w/w) and about 1.0% (w/w). In one embodiment, erythritol is present at a concentration of about 0.25% (w/w). In one embodiment, levocarnitine is present at a concentration of about 0.25% (w/w). In one embodiment, erythritol is present at a concentration of about 0.25% (w/w), and levocarnitine is present at a concentration of about 0.25% (w/w).

Further to any embodiment described above, in one embodiment the low salt ophthalmic pharmaceutical composition further includes one or more tonicity agents. It is understood that a tonicity agent, e.g., glycerin, can also function as a demulcent. Thus, in one embodiment the tonicity of the low salt ophthalmic pharmaceutical composition is a demulcent.

In one embodiment, the tonicity agents of the low salt ophthalmic pharmaceutical composition is glycerin present at a concentration between about 0.01% (w/w) and about 5.0% (w/w). In one embodiment, glycerin is present at a concentration of about 1.0% (w/w).

Further to any embodiment described above, in one embodiment the low salt ophthalmic pharmaceutical composition further includes a preservative. Exemplary preservatives employed in topic ophthalmic pharmaceutical compositions include quaternary ammonium (e.g., benzalkonium chloride, polyquaternium-1, and the like), mercurials (e.g., thimerosol), alcohols (e.g., chlorobutanol, benzyl alcohol, and the like), carboxylic acids (e.g., sorbic acid and the like), phenols (methyl or propyl parabens), amidines (e.g., chlorhexidine), and other compounds (e.g., stabilized oxychloro complex). An exemplary stabilized oxychloro complex is Purite® (Purite Ltd, Oxon, UK).

In one embodiment, the low salt ophthalmic pharmaceutical composition includes a stabilized oxychloro complex. In one embodiment, the stabilized oxychloro complex is present at a concentration between about 0.001% (w/w) and about 0.1% (w/w). In one embodiment, the stabilized oxychloro complex is present at a concentration of about 0.01% (w/w).

Further to any embodiment described above, in one embodiment the low salt ophthalmic pharmaceutical composition further includes a buffer. Exemplary buffers useful in the compositions disclosed herein include inorganic acids (e.g., borate, phosphate, and the like), organic acids (e.g., lower alkyl carboxylic acids), and amines including primary, secondary, tertiary and quaternary amines as known in the art. The term "lower alkyl carboxylic acid" refers to $C_1$-$C_6$ alkyl having at least one —COOH substituent.

In one embodiment of the low salt ophthalmic pharmaceutical composition, the buffer is boric acid present at a concentration between about 0.01% (w/w) and about 1.0% (w/w). In one embodiment, boric acid is present at a concentration of about 0.6% (w/w).

Further to any embodiment described above, in one embodiment the low salt ophthalmic pharmaceutical composition further includes a pH adjustment agent. Exemplary pH adjustment agents include strong acids (e.g., HCl) and strong bases (e.g., NaOH). In one embodiment, the pH adjustment agent is NaOH. In one embodiment, the pH of the low salt ophthalmic pharmaceutical composition is in the range of about pH 7 to pH 8. In one embodiment, the pH of the low salt ophthalmic pharmaceutical composition is about pH 7.3.

Further to any embodiment described above, in one embodiment low salt ophthalmic pharmaceutical composition includes castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water. See Table 1. With reference to Tables 1 and 2, the term "q.s." refers in the customary sense to a sufficient amount to afford the nominal amount or pH.

TABLE 1

Range of components of low salt ophthalmic pharmaceutical composition.

| Component | Range of Approximate Amounts | Units | Function |
|---|---|---|---|
| Polysorbate 80 | 0.01 to 1.0 | % (w/w) | Surfactant |
| Carboxymethyl cellulose sodium | 0.01 to 1.0 | % (w/w) | Polymer lubricant |
| Glycerin | 0.01 to 5.0 | % (w/w) | Tonicity agent |
| stabilized oxychloro complex | 0.001 to 0.1 | % (w/w) | Preservative |
| Boric acid | 0.6 | % (w/w) | Buffer |
| Acrylate/$C_{10}$-$C_{30}$ acrylate crosspolymer (Pemulen ™ TR-2) | 0.01 to 1.0 | % (w/w) | Salt-sensitive viscosity modulating polymer |
| Castor oil | 0.01 to 10 | % (w/w) | Therapeutic lipid |
| Erythritol | 0.25 | % (w/w) | Compatible solute |
| Levocarnitine | 0.25 | % (w/w) | Compatible solute |
| NaOH | q.s. to pH 7.3 | pH | QS Adjustment |
| Water for injection | q.s. to 100% | % (w/w) | QS Adjustment |

In one embodiment, the low salt ophthalmic pharmaceutical composition has a formulation as set forth in Table 2 following.

TABLE 2

Exemplary low salt ophthalmic pharmaceutical composition.

| Component | Range of Approximate Amounts | Units | Function |
|---|---|---|---|
| Polysorbate 80 | 0.5 | % (w/w) | Surfactant |
| Carboxymethyl cellulose sodium | 0.5 | % (w/w) | Polymer lubricant |
| Glycerin | 1.0 | % (w/w) | Tonicity agent |
| stabilized oxychloro complex | 0.01 | % (w/w) | Preservative |
| Boric acid | 0.6 | % (w/w) | Buffer |
| Acrylate/$C_{10}$-$C_{30}$ acrylate crosspolymer (Pemulen ™ TR-2) | 0.1 | % (w/w) | Salt-sensitive viscosity modulating polymer |
| Castor oil | 0.25 | % (w/w) | Therapeutic lipid |
| Erythritol | 0.25 | % (w/w) | Compatible solute |
| Levocarnitine | 0.25 | % (w/w) | Compatible solute |
| NaOH | q.s. to pH 7.3 | pH | QS Adjustment |
| Water for injection | q.s. to 100% | % (w/w) | QS Adjustment |

IV. Methods of Use

In another aspect, there is provided a method for treating dry eye syndrome. The method includes administering to a subject in need of treatment of dry eye syndrome a therapeutically effective amount of a low salt ophthalmic pharmaceutical composition as disclosed herein, thereby treating dry eye syndrome in the subject. In one embodiment, the low salt ophthalmic pharmaceutical composition includes a sub-micron emulsion, a polymer lubricant, and a salt-sensitive viscosity modulating polymer, as disclosed herein, wherein the sub-micron emulsion includes a surfactant and a therapeutic lipid.

In one embodiment, the therapeutic lipid within the low salt ophthalmic pharmaceutical composition is castor oil at a concentration between about 0.01% (w/w) and about 10% (w/w).

In one embodiment, the surfactant is polysorbate 80 at a concentration between about 0.01% (w/w) and about 1.0% (w/w).

In one embodiment, the salt-sensitive viscosity modulating polymer includes acrylate/C10-C30 acrylate crosspolymer present at a concentration between about 0.01% (w/w) and about 1.0% (w/w). In one embodiment, the salt-sensitive viscosity modulating polymer has a standard emulsion viscosity between 1,700 and 4,500 cPs.

In one embodiment, the polymer lubricant is carboxymethylcellulose sodium present at a concentration between about 0.01% (w/w) and about 1.0% (w/w).

In one embodiment, the low salt ophthalmic pharmaceutical composition further includes a compatible solute. In one embodiment, the compatible solute is erythritol at a concentration of about 0.25% (w/w) and levocarnitine at a concentration of about 0.25% (w/w).

In one embodiment, the low salt ophthalmic pharmaceutical composition further includes a tonicity agent. In one embodiment, the tonicity agent is glycerin at a concentration between about 0.01% (w/w) and about 5.0% (w/w).

In one embodiment, the low salt ophthalmic pharmaceutical composition further includes a preservative. In one embodiment, the preservative is a stabilize oxychloro compound present at a concentration between about 0.001% (w/w) and about 0.1% (w/w).

In one embodiment, the low salt ophthalmic pharmaceutical composition further includes a buffer. In one embodiment, the buffer is boric acid present at a concentration of about 0.6% (w/w).

In one embodiment, the low salt ophthalmic pharmaceutical composition further includes a pH adjustment agent. In one embodiment, the pH adjustment agent is NaOH.

In one embodiment, the low salt ophthalmic pharmaceutical composition has a pH of about 7.3

In one embodiment, the low salt ophthalmic pharmaceutical composition includes the components as set forth in Table 1. In one embodiment, the low salt ophthalmic pharmaceutical composition includes the components as set forth in Table 2.

V. EXAMPLES

Example 1

Effect of Dilution on Viscosity With and Without Salt

Introduction. A low salt ophthalmic pharmaceutical composition was formulated to deliver therapeutic lipid and lubricating polymers to the precorneal tear fluid. A salt-sensitive viscosity modulating polymer, as disclosed herein, was used to stabilize the lipid in solution yet allow efficient lipid delivery on the eye when mixed with salts in the tear film upon instillation. Delivery of therapeutic lipid to the lipid layer of the tear film was modeled by diluting the low salt ophthalmic pharmaceutical composition with a salt solution and measuring the associated change in viscosity and lipid distribution. As control, the results were compared with a marketed emulsion eye drop lacking salt-sensitive viscosity modulating polymer. The term "sample" in this section refers to a low salt ophthalmic pharmaceutical composition as set forth in Table 2 above. The term "control" refers to a marketed emulsion eye drop lacking salt-sensitive viscosity modulating polymer.

Methods. Viscosity change measurements employed a Brookfield viscometer (25° C., spindle 18, 30 rpm) (Brookfield Engineering laboratories, Middleboro, Mass.), before and after dilution of sample 1:1 with water or salt solution ranging from 30 to 600 mOsm NaCl.

Viscosity measurements were repeated with concentrated NaCl to confirm initial results.

Results. As depicted in FIG. 1A, the viscosity of the tested sample decreased monotonically as a function of salt concentration. When diluted 1:1 with water, the viscosity of the sample was reduced by about 51%. When diluted 1:1 with 30 to 600 mOsm NaCl, the viscosity loss was 62.7% to 78.0%.

In contrast, the control composition displayed equivalent reduction in viscosity upon dilution with either water to salt solution.

Figure 1B:
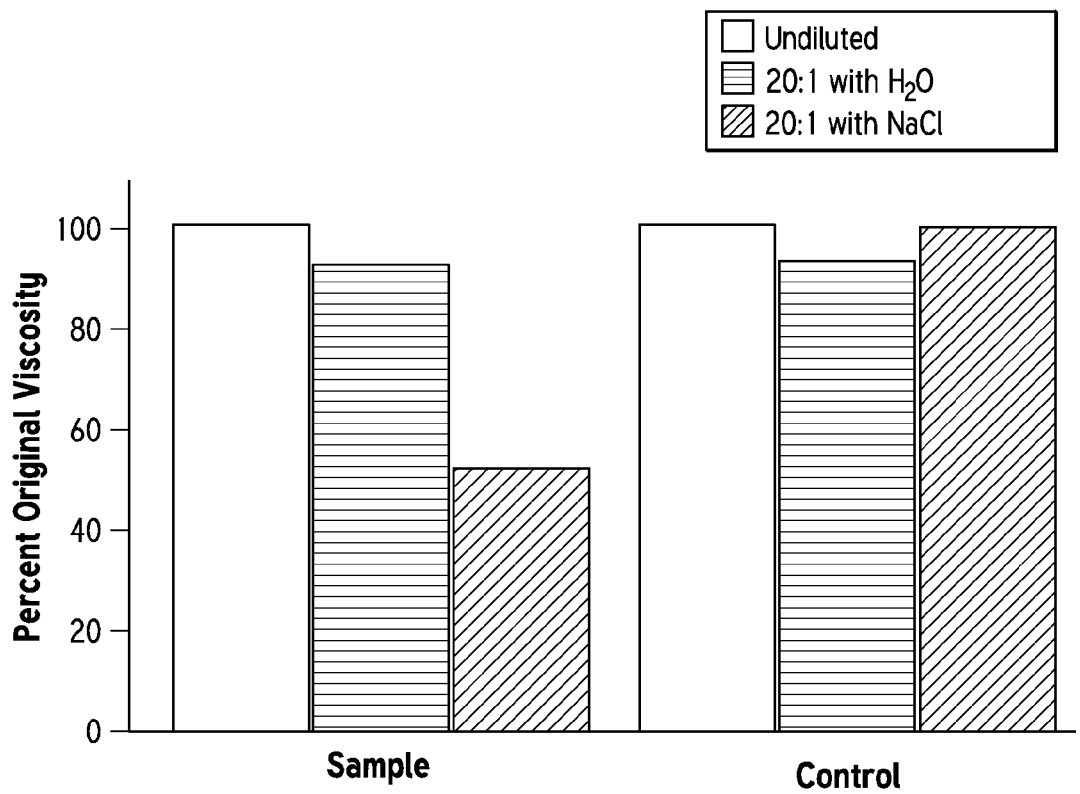
FIG. 1B depicts a histogram of percent change in viscosity upon dilution with water and salt for the sample and control described in Example 1. Legend (left to right): undiluted (open); diluted 20:1 with water (horizontal stripes); diluted 20:1 with 9% NaCl (diagonal stripes).

As shown in FIG. 1B, dilution of the sample of low salt ophthalmic pharmaceutical composition at 20:1 with water or 9% NaCl afforded a percent change reduction in viscosity of about 9% or about 49%, respectively. In contrast, dilution of the control eye drop composition resulted in a percent change reduction in viscosity of about 8% and 1%, respectively, for dilution 20:1 with water and 9% NaCl.

Summary. The viscosity reduction upon increased salt concentration in a sample low salt ophthalmic pharmaceutical composition was greater than observed for the control eye drop lacking salt-sensitive viscosity modulating polymer. The greatest viscosity difference for the sample was observed between dilution with water and dilution with 37 mOsm NaCl. In contrast, the viscosity of the control was observed to correlate only with dilution and not with salt concentration.

Example 2

Effect of Stability of Water and Salt Concentration

Introduction. The stability and uniformity of the emulsions described in Example 1 was investigated under undiluted and diluted conditions.

Methods. Assessment of stability and uniformity of sample compositions employed a time-controlled centrifuge with integrated optical detector (Lumisizer®, L.U.M. GmbH, Berlin, Germany). Samples were undiluted, or diluted 1:20 with water or concentrated (9%) NaCl resulting in a final concentration of 0.45% NaCl simulating the saline concentration of a drop of ophthalmic pharmaceutical composition on the tear film. Concentrated NaCl was used to minimize the dilution effect on light transmittance. Scans were taken repetitively for 2-min at 4000 rpm.

Figure 2A:
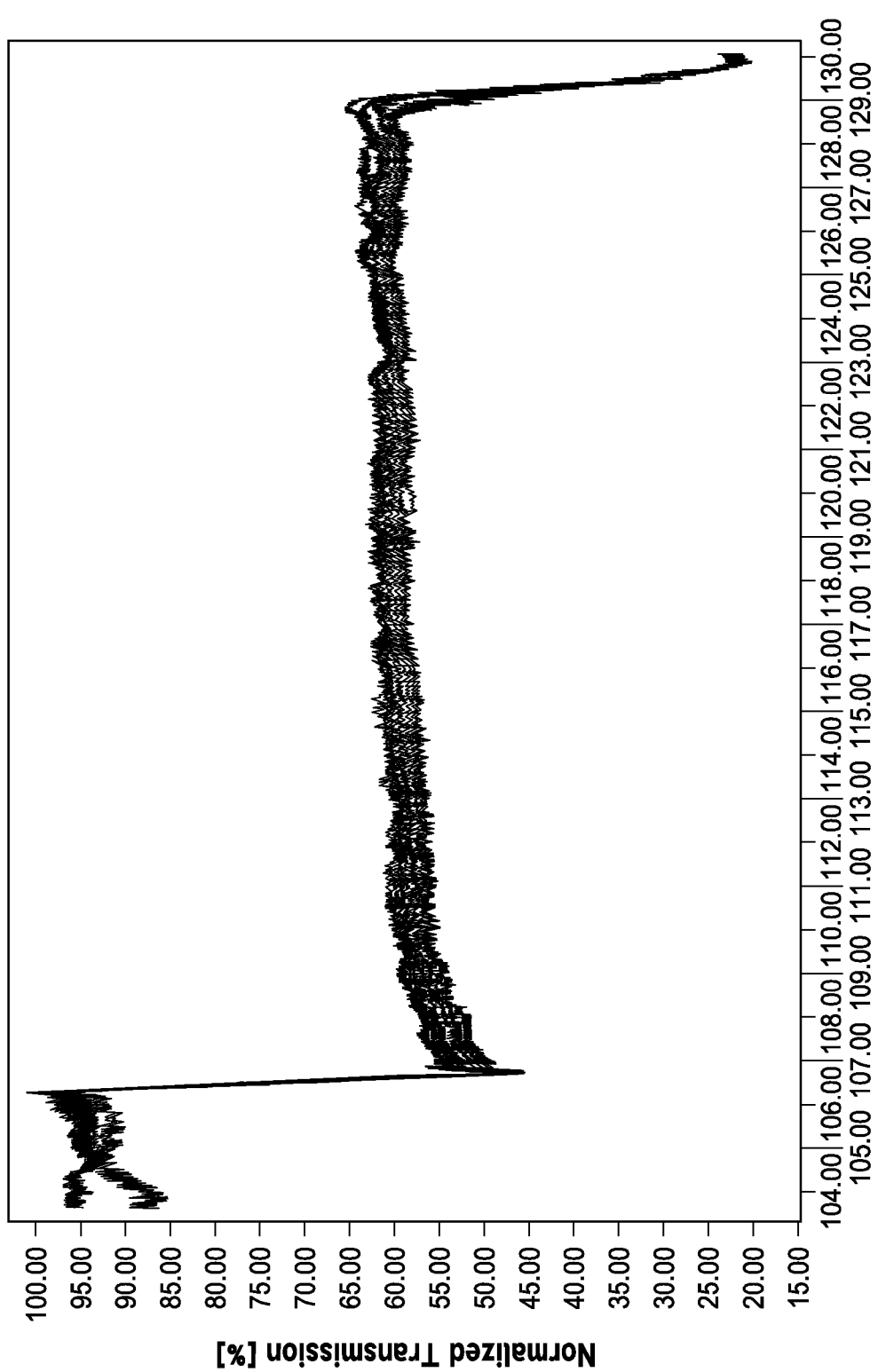
FIGS. 2A-2B depict overlaid real-time integrated optical detector scans in a time-controlled centrifuge of undiluted sample (FIG. 2A) and control (FIG. 2B) as described in Example 2. Legend: X-axis: position (mm) along the centrifugal chamber; Y-axis: light transmissions (% T).
Figure 2B:
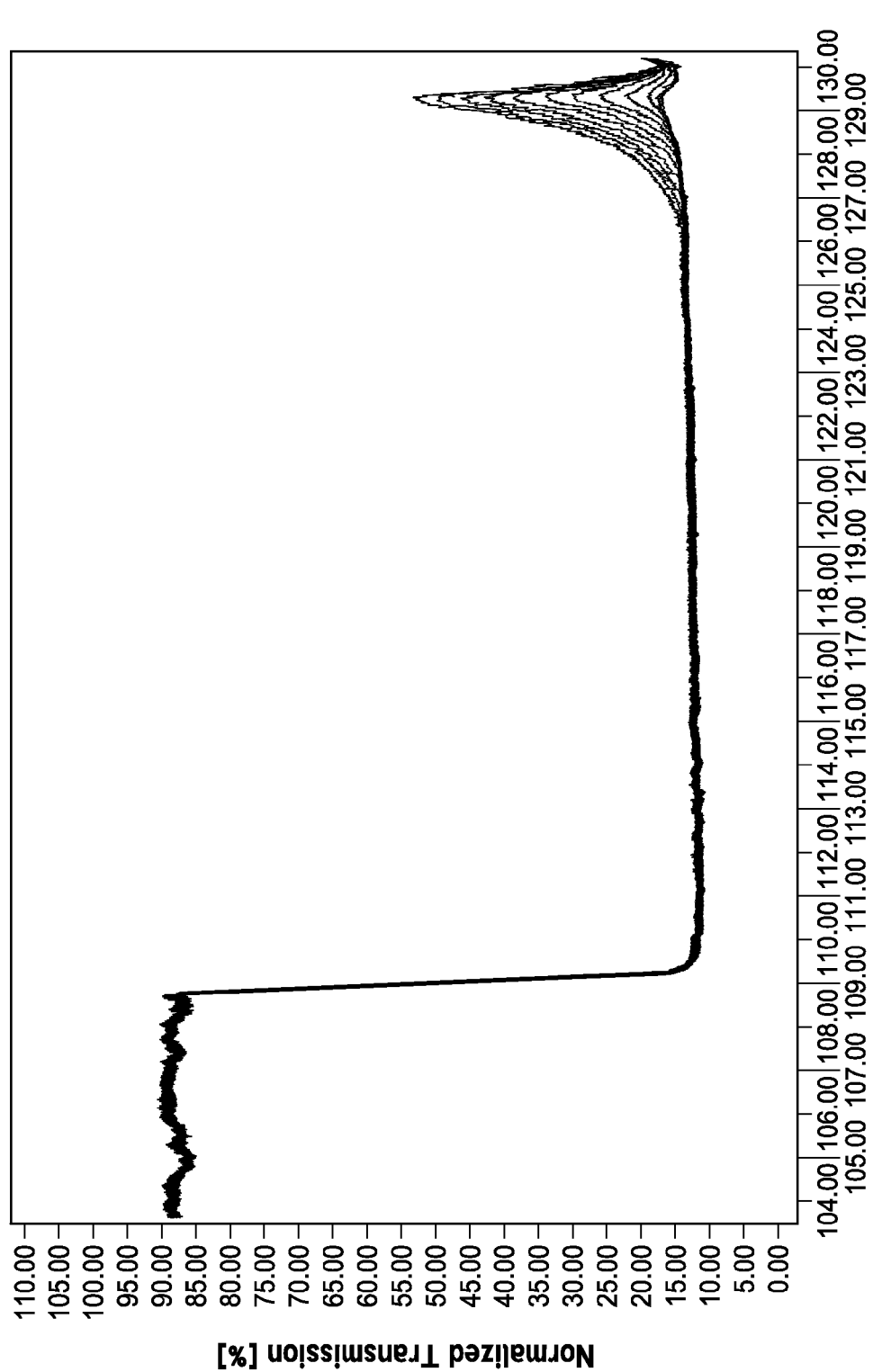

Results. As shown in FIG. 2A, an undiluted sample of the low salt ophthalmic pharmaceutical composition is stable with time. Light transmission (% T) for the sample is approximately 55%. In contrast, as shown in FIG. 2B, the undiluted control eye drop lacking salt-sensitive viscosity modulating polymer is slightly unstable as indicated by the change over time at the distal end of the integrated optical detector of the time-controlled centrifuge. Moreover, the light transmission in the control is significantly lower, having a value of about 12% (% T) prior to the changes which accompany the destabilization of the control. Without wishing to be bound by any theory, it is believed that changes in % T correlate with release of lipid which migrates to the top (i.e., distal end) of the centrifuge chamber, consistent with floating of lipid to the air interface of the aqueous layer of the tear film.

Figure 3A:
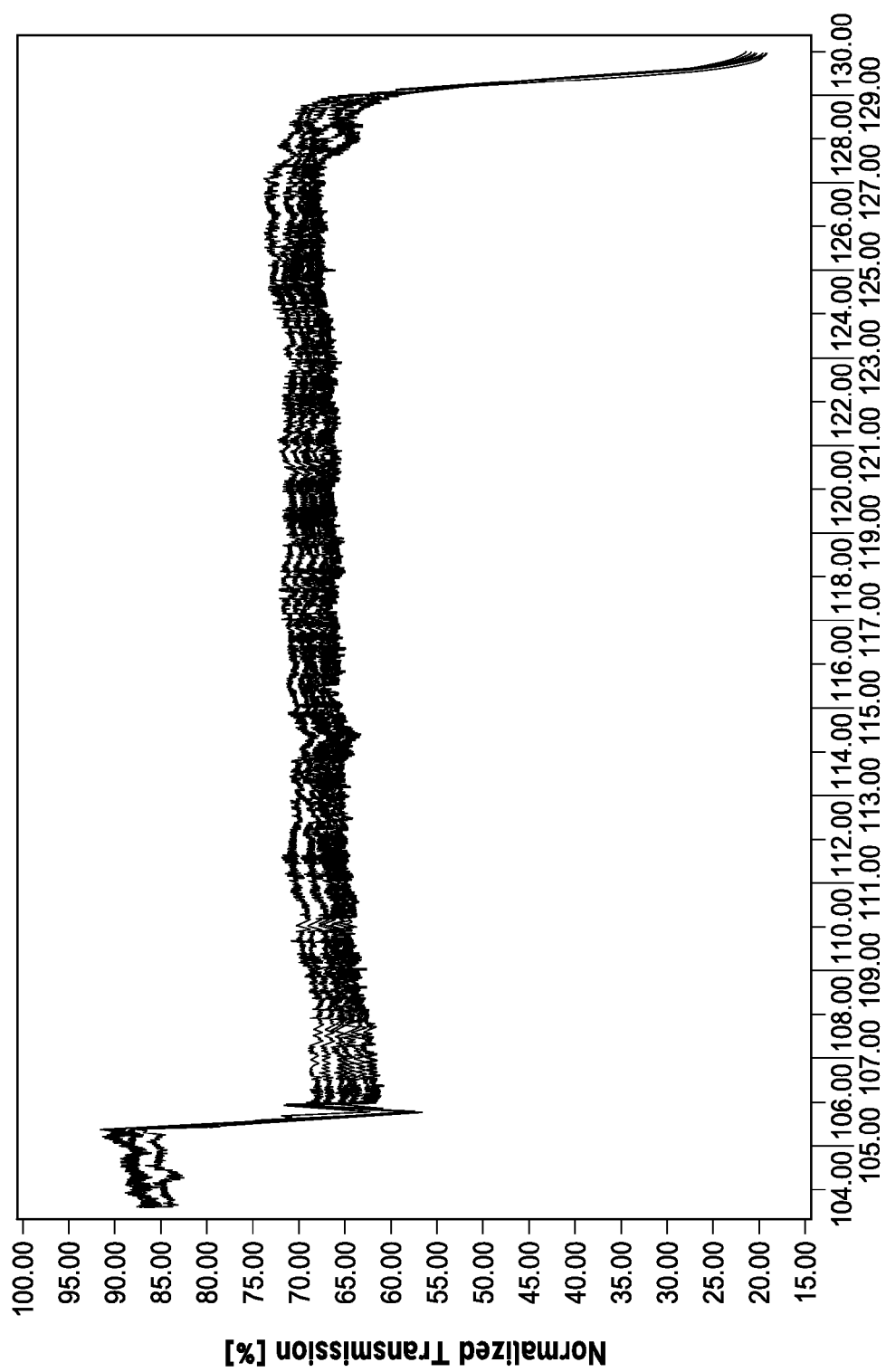
FIGS. 3A-3B depict overlaid real-time integrated optical detector scans in a time-controlled centrifuge of sample (FIG. 3A) and control (FIG. 3B) diluted 1:20 with water, as described in Example 2. Legend: as in FIGS. 2A-2B.
Figure 3B:
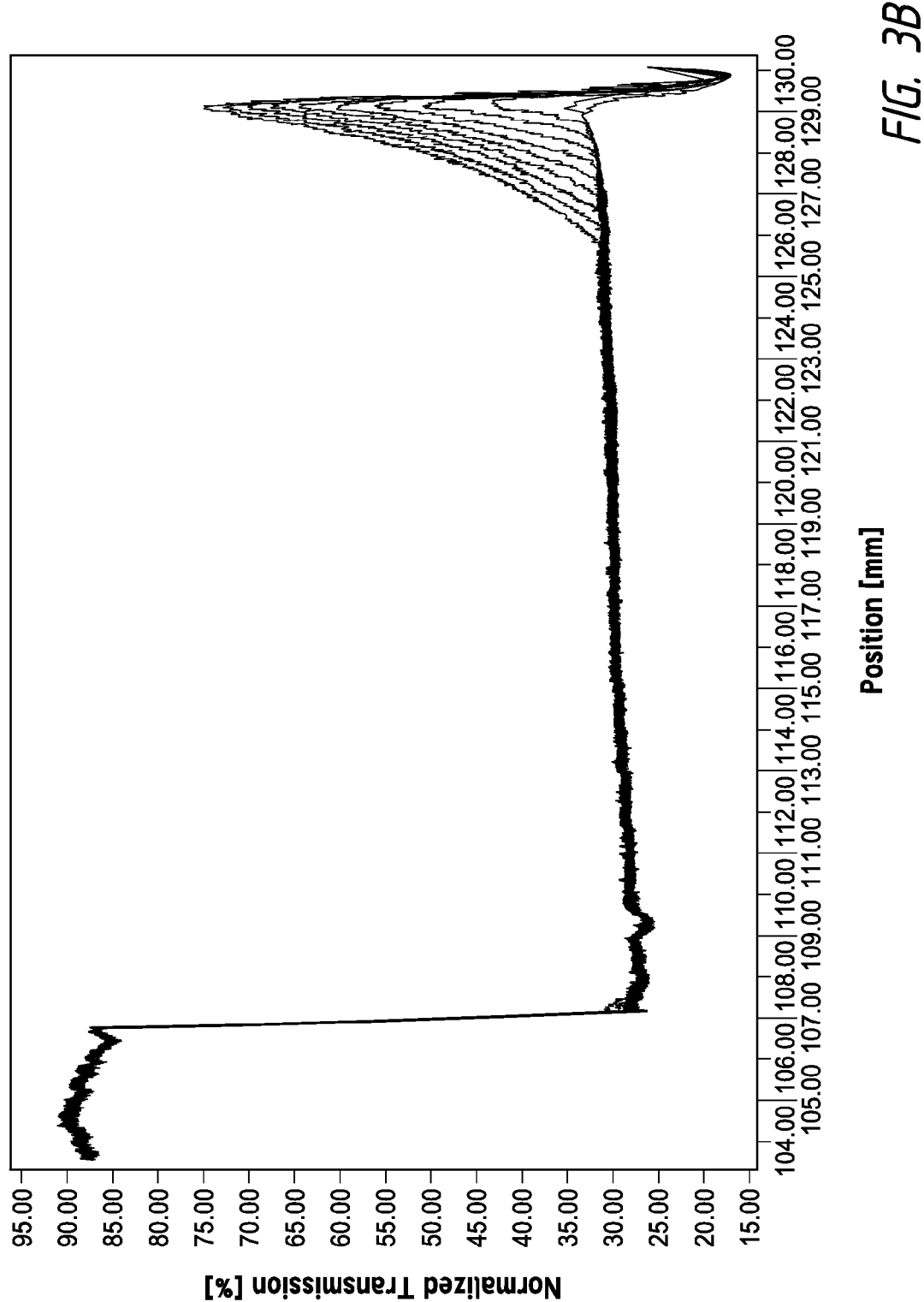

As shown in FIGS. 3A-3B, upon dilution 1:20 with water, both the sample and control show increase in % T due to dilution. Stability in both experiments is similar to that observed in the undiluted state.

Figure 4A:
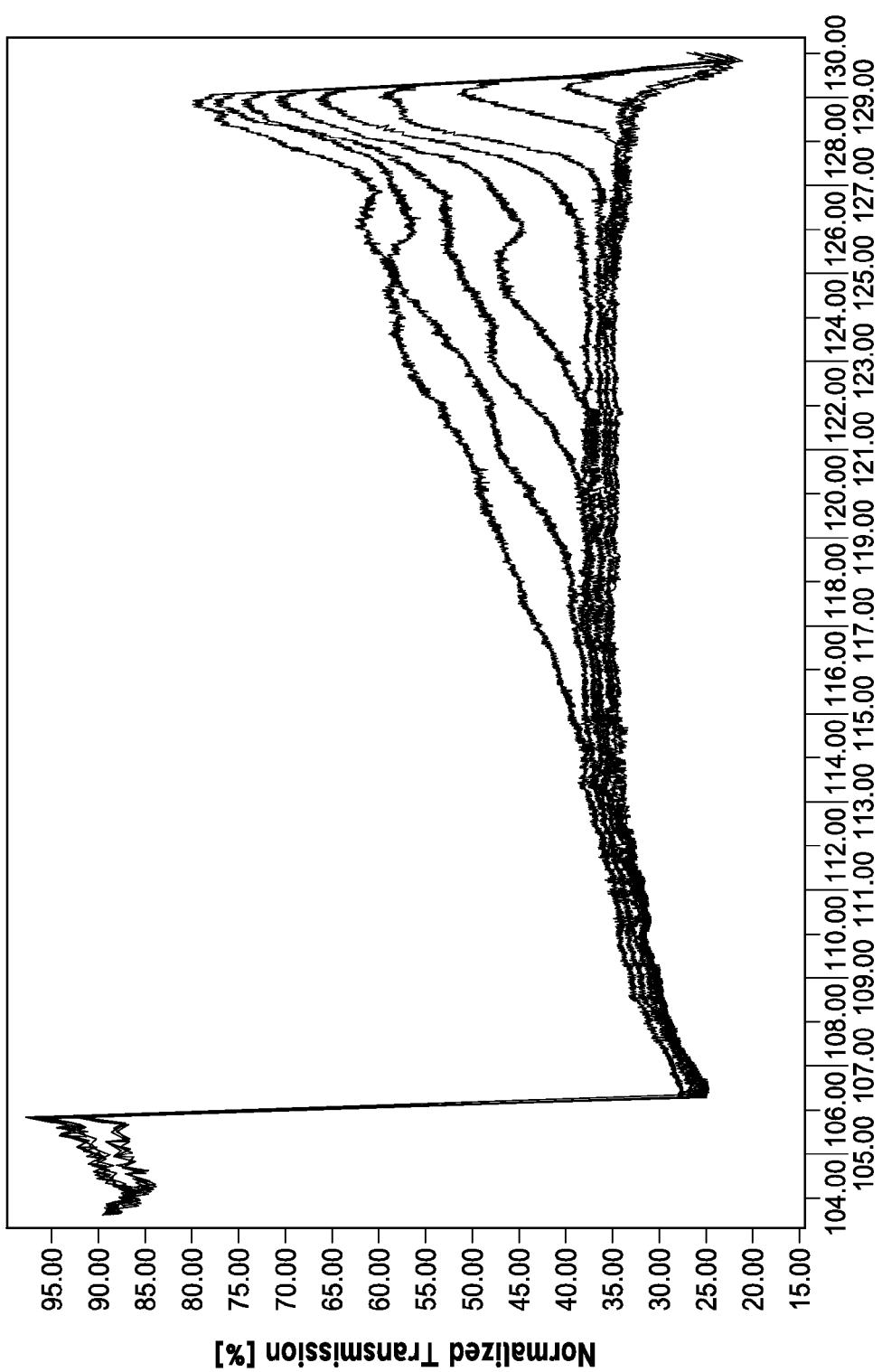
FIGS. 4A-4B depict overlaid real-time integrated optical detector scans in a time-controlled centrifuge of sample (FIG. 4A) and control (FIG. 4B) diluted 1:20 with 9% NaCl solution, as described in Example 2. Legend: as in FIGS. 2A-2B.
Figure 4B:
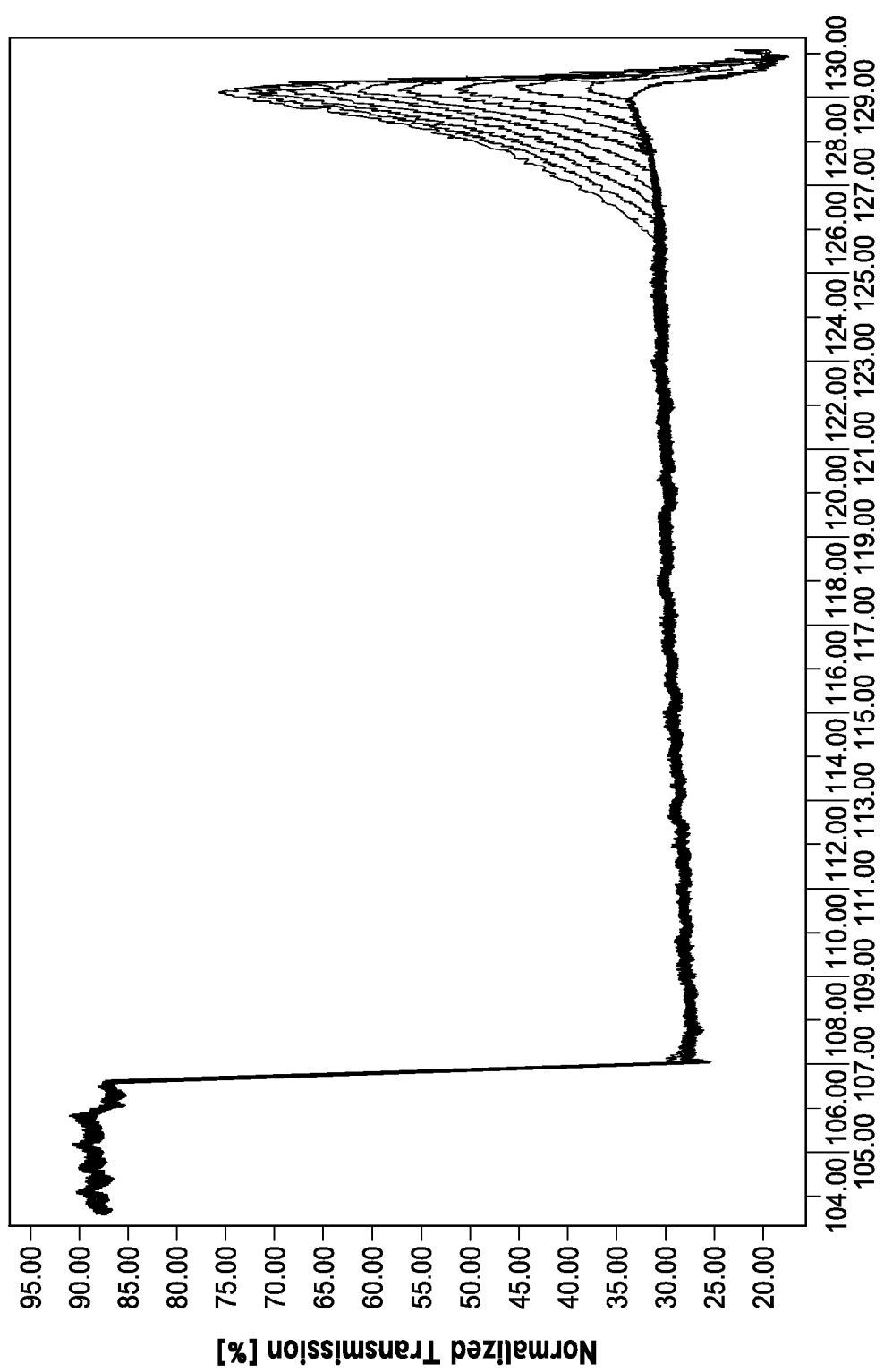

As shown in FIG. 4A, upon dilution 1:20 with 9% NaCl, the sample is significantly destabilized with rapid release of oil and transient drop in % T. In contrast, as shown in FIG. 4B, the stability of the control is similar to that observed with water dilution.

Summary. The low salt ophthalmic pharmaceutical composition sample was stable and uniform in the undiluted state, as occurs in storage prior to use. This demonstrates the surprising benefit of excellent stability and uniformity in storage, while requiring no shaking of the composition prior to instillation. In contrast, the control eye drop lacking salt-sensitive viscosity modulating polymer is slightly unstable in storage. When mixed with salt, the viscosity of the sample dropped significantly. In contrast, the control did not demonstrate a dependence of stability on salt concentration. Without wishing to be bound by any theory, it is believed that the reduction in viscosity in the sample destabilizes the structure of the emulsion, resulting in release of lipid. Accordingly, the use of a salt-sensitive viscosity modulating polymer within the sample increases delivery of lipids at the ocular target.

Example 3

Lipid Droplet Particle Size Upon Dilution with Salt

Introduction. Lipid particle size in solution can be determined by a variety of techniques known in the art, including e.g., laser diffraction, dynamic image analysis, static image analysis, and dynamic light scattering. The change in lipid droplet size within formulations disclosed herein upon instillation in the eye was determine in model systems by dilution with salt solution.

Methods. Average particle size (lipid droplet size) was determined using a Horiba particle size analysis system (Horiba, Ltd., Fukuoka Japan). The sample composition and salt solutions were as described in Examples 1-2.

Results. Upon dilution with salt solution, the average particle size (i.e., lipid droplet size) was unchanged (data not shown).

Summary. The lipid droplet size of tested formulations does not change upon an increase in salt concentration. Accordingly, the lipid droplets remain sufficiently small to provide effective incorporation of lipid into the tear film.

Example 4

Clinical Studies

Introduction. Tear breakup time (TBUT) is recognized as a useful procedure in the diagnosis of dry eye syndrome and related conditions. As known in the art, compositions and methods which increase TBUT can be beneficial in the treatment. Thus, clinical studies were conducted which measured TBUT for a low salt ophthalmic pharmaceutical composition disclosed herein. Moreover, the clinical studies included tolerability and comfort assessments, as known in the art.

Methods. The fluorescein tear breakup time procedure was employed, as known in the art.

Results. The low salt ophthalmic pharmaceutical composition set forth in Table 2 above was observed to prolong TBUT. Moreover, the composition demonstrates clinical tolerability and comfort.

VI. Embodiments

Embodiments of the compositions and methods disclosed herein include, but are not limited to, the following:

Embodiment 1. A low salt ophthalmic pharmaceutical composition comprising a sub-micron emulsion, a polymer lubricant, and a salt-sensitive viscosity modulating polymer, wherein said sub-micron emulsion comprises a surfactant and a therapeutic lipid.

Embodiment 2. The low salt ophthalmic pharmaceutical composition of embodiment 1, wherein said composition is clear.

Embodiment 3. The low salt ophthalmic pharmaceutical composition according to any one of embodiments 1 to 2, wherein said therapeutic lipid is a fatty acid glyceride.

Embodiment 4. The low salt ophthalmic pharmaceutical composition according to embodiment 3, wherein said fatty acid glyceride is a castor oil, olive oil, peanut oil, corn oil, or sunflower oil.

Embodiment 5. The low salt ophthalmic pharmaceutical composition according to any one of embodiments 1 to 4, wherein said therapeutic lipid is castor oil.

Embodiment 6. The low salt ophthalmic pharmaceutical composition according to embodiment 5, wherein said castor oil is present at a concentration between about 0.01% (w/w) and about 10% (w/w).

Embodiment 7. The low salt ophthalmic pharmaceutical composition according to embodiment 6, wherein said castor oil is present at a concentration of about 0.25% (w/w).

Embodiment 8. The low salt ophthalmic pharmaceutical composition according to any one of embodiments 1 to 7, wherein said surfactant is a sorbitan ester.

Embodiment 9. The low salt ophthalmic pharmaceutical composition according to embodiment 8, wherein said surfactant is polysorbate 80.

Embodiment 10. The low salt ophthalmic pharmaceutical composition according to embodiment 9, wherein said polysorbate 80 is present at a concentration between about 0.01% (w/w) and about 1.0% (w/w).

Embodiment 11. The low salt ophthalmic pharmaceutical composition according to embodiment 10, wherein said polysorbate 80 is present at a concentration of about 0.5% (w/w).

Embodiment 12. The low salt ophthalmic pharmaceutical composition according to any one of embodiments 1 to 11, wherein said salt-sensitive viscosity modulating polymer is an acrylate/C10-C30 acrylate crosspolymer.

Embodiment 13. The salt-sensitive viscosity modulating polymer according to embodiment 12 having a standard emulsion viscosity between 1,700 and 4,500 cPs.

Embodiment 14. The low salt ophthalmic pharmaceutical composition according to embodiment 13, wherein said salt-sensitive viscosity modulating polymer is present at a concentration between about 0.01% (w/w) and about 1.0% (w/w).

Embodiment 15. The low salt ophthalmic pharmaceutical composition according to embodiment 14, wherein said salt-sensitive viscosity modulating polymer is present at a concentration of about 0.1% (w/w).

Embodiment 16. The low salt ophthalmic pharmaceutical composition according to any one of embodiments 1 to 15, wherein said polymer lubricant is a demulcent.

Embodiment 17. The low salt ophthalmic pharmaceutical composition according to embodiment 16, wherein said polymer lubricant is carboxymethylcellulose sodium present at a concentration between about 0.01% (w/w) and about 1.0% (w/w).

Embodiment 18. The low salt ophthalmic pharmaceutical composition according to embodiment 17, wherein said carboxymethylcellulose sodium is present at a concentration of about 0.5% (w/w).

Embodiment 19. The low salt ophthalmic pharmaceutical composition according to any one of embodiments 1 to 18, further comprising a compatible solute.

Embodiment 20. The low salt ophthalmic pharmaceutical composition according to embodiment 19, wherein said compatible solute is a polyol or a zwitterionic amino acid.

Embodiment 21. The low salt ophthalmic pharmaceutical composition according to embodiment 20, wherein said compatible solute is erythritol or levocarnitine.

Embodiment 22. The low salt ophthalmic pharmaceutical composition according to embodiment 21, wherein said compatible solute is erythritol present at a concentration between about 0.01% (w/w) and about 1.0% (w/w).

Embodiment 23. The low salt ophthalmic pharmaceutical composition according to embodiment 21, wherein said compatible solute is levocarnitine present at a concentration between about 0.01% (w/w) and about 1.0% (w/w).

Embodiment 24. The low salt ophthalmic pharmaceutical composition according to embodiment 21, wherein said compatible solute is erythritol at a concentration of about 0.25% (w/w).

Embodiment 25. The low salt ophthalmic pharmaceutical composition according to embodiment 21, wherein said compatible solute is levocarnitine at a concentration of about 0.25% (w/w).

Embodiment 26. The low salt ophthalmic pharmaceutical composition according to embodiment 21 comprising erythritol at a concentration of about 0.25% (w/w) and levocarnitine at a concentration of about 0.25% (w/w).

Embodiment 27. The low salt ophthalmic pharmaceutical composition according to any one of embodiments 1 to 26, further comprising a tonicity agent.

Embodiment 28. The low salt ophthalmic pharmaceutical composition according to embodiment 27, wherein said tonicity agent is a demulcent.

Embodiment 29. The low salt ophthalmic pharmaceutical composition according to embodiment 27, wherein said tonicity agent is glycerin present at a concentration between about 0.01% (w/w) and about 5.0% (w/w).

Embodiment 30. The low salt ophthalmic pharmaceutical composition according to embodiment 29, wherein said glycerin is present at a concentration of about 1.0% (w/w).

Embodiment 31. The low salt ophthalmic pharmaceutical composition according to any one of embodiments 1 to 30, further comprising a preservative.

Embodiment 32. The low salt ophthalmic pharmaceutical composition according to embodiment 31, wherein said preservative is a stabilized oxychloro complex.

Embodiment 33. The low salt ophthalmic pharmaceutical composition according to embodiment 32, wherein said preservative is present at a concentration between about 0.001% (w/w) and about 0.1% (w/w).

Embodiment 34. The low salt ophthalmic pharmaceutical composition according to embodiment 33, wherein said preservative is present at a concentration of about 0.01% (w/w).

Embodiment 35. The low salt ophthalmic pharmaceutical composition according to any one of embodiments 1 to 34, further comprising a buffer.

Embodiment 36. The low salt ophthalmic pharmaceutical composition according to embodiment 35, wherein said buffer is boric acid present at a concentration between about 0.01% (w/w) and about 1.0% (w/w).

Embodiment 37. The low salt ophthalmic pharmaceutical composition according to embodiment 36, wherein said boric acid is present at a concentration of about 0.6% (w/w).

Embodiment 38. The low salt ophthalmic pharmaceutical composition according to any one of embodiments 1 to 37, further comprising a pH adjustment agent.

Embodiment 39. The low salt ophthalmic pharmaceutical composition according to embodiment 38, wherein said pH adjustment agent is NaOH.

Embodiment 40. The low salt ophthalmic pharmaceutical composition according to embodiment 38 having pH about 7.3

Embodiment 41. The low salt ophthalmic pharmaceutical composition according to embodiment 39 comprising: castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water.

Embodiment 42. A low salt ophthalmic pharmaceutical composition comprising: castor oil at a concentration of about 0.25% (w/w); polysorbate 80 at a concentration of about 0.5% (w/w); acrylate/C10-C30 acrylate crosspolymer at a concentration of about 0.1% (w/w), wherein said acrylate/C10-C30 acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.

Embodiment 43. A method for treating dry eye syndrome comprising: administering to a subject in need of treatment of dry eye syndrome a low salt ophthalmic pharmaceutical composition according to any one of embodiments 1 to 42; thereby treating said dry eye syndrome.

Embodiment 44. The method of embodiment 43, wherein said therapeutic lipid is castor oil at a concentration between about 0.01% (w/w) and about 10% (w/w).

Embodiment 45. The method of any one of embodiments 43 to 44, wherein said surfactant is polysorbate 80 at a concentration between about 0.01% (w/w) and about 1.0% (w/w).

Embodiment 46. The method of any one of embodiments 43 to 45, wherein said salt-sensitive viscosity modulating polymer comprises acrylate/C10-C30 acrylate crosspolymer present at a concentration between about 0.01% (w/w) and about 1.0% (w/w), wherein said salt-sensitive viscosity modulating polymer has a standard emulsion viscosity between 1,700 and 4,500 cPs.

Embodiment 47. The method of any one of embodiments 44 to 46, wherein said polymer lubricant is carboxymethylcellulose sodium present at a concentration between about 0.01% (w/w) and about 1.0% (w/w).

Embodiment 48. The method of any one of embodiments 43 to 47, further comprising a compatible solute, wherein said compatible solute is erythritol at a concentration of about 0.25% (w/w) and levocarnitine at a concentration of about 0.25% (w/w).

Embodiment 49. The method of any one of embodiments 43 to 48, further comprising a tonicity agent, wherein said tonicity agent is glycerin at a concentration between about 0.01% (w/w) and about 5.0% (w/w).

Embodiment 50. The method of any one of embodiments 43 to 49, further comprising a preservative, wherein said preservative is a stabilize oxychloro compound present at a concentration between about 0.001% (w/w) and about 0.1% (w/w).

Embodiment 51. The method of any one of embodiments 43 to 50, further comprising a buffer, wherein said buffer is boric acid present at a concentration of about 0.6% (w/w).

Embodiment 52. The method of any one of embodiments 43 to 51, further comprising a pH adjustment agent, wherein said pH adjustment agent is NaOH.

Embodiment 53. The method of any one of embodiments 43 to 52, said low salt ophthalmic pharmaceutical composition having pH of about 7.3.

Embodiment 54. The method of embodiment 54, wherein said low salt ophthalmic pharmaceutical composition comprises: castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water.

Embodiment 55. The method of embodiment 54, wherein said low salt ophthalmic pharmaceutical composition comprises: castor oil at a concentration of about 0.25% (w/w); polysorbate 80 at a concentration of about 0.5% (w/w); acrylate/C10-C30 acrylate crosspolymer at a concentration of about 0.1% (w/w), wherein said acrylate/C10-C30 acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.

What is claimed is:

1. A low salt ophthalmic pharmaceutical composition comprising a sub-micron emulsion, a polymer lubricant, and a salt-sensitive viscosity modulating polymer, wherein said sub-micron emulsion comprises a surfactant and a therapeutic lipid consisting essentially of castor oil.

2. The low salt ophthalmic pharmaceutical composition according to claim 1, wherein said therapeutic lipid is castor oil present at a concentration of about 0.25% (w/w).

3. The low salt ophthalmic pharmaceutical composition according to claim 1, wherein said surfactant is a sorbitan ester, wherein said sorbitan ester is polysorbate 80 present at a concentration of about 0.5% (w/w).

4. The low salt ophthalmic pharmaceutical composition according to claim 1, wherein said salt-sensitive viscosity modulating polymer is an acrylate/$C_{10}$-$C_{30}$ acrylate crosspolymer having a standard emulsion viscosity between 1,700 and 4,500 cPs, wherein said salt-sensitive viscosity modulating polymer is present at a concentration of about 0.1% (w/w).

5. The low salt ophthalmic pharmaceutical composition according to claim 1, wherein said polymer lubricant is carboxymethylcellulose sodium present at a concentration of about 0.5% (w/w).

6. The low salt ophthalmic pharmaceutical composition according to claim 1, further comprising a compatible solute.

7. The low salt ophthalmic pharmaceutical composition according to claim 6, wherein said compatible solute is erythritol or levocarnitine.

8. The low salt ophthalmic pharmaceutical composition according to claim 7 comprising erythritol at a concentration of about 0.25% (w/w) and levocarnitine at a concentration of about 0.25% (w/w).

9. The low salt ophthalmic pharmaceutical composition according to claim 1, further comprising a tonicity agent, wherein said tonicity agent is glycerin present at a concentration of about 1.0% (w/w).

10. The low salt ophthalmic pharmaceutical composition according to claim 1, further comprising a preservative.

11. The low salt ophthalmic pharmaceutical composition according to claim 10, wherein said preservative is a stabilized oxychloro complex present at a concentration of about 0.01% (w/w).

12. The low salt ophthalmic pharmaceutical composition according to claim 1, further comprising a buffer.

13. The low salt ophthalmic pharmaceutical composition according to claim 12, wherein said buffer is boric acid present at a concentration of about 0.6% (w/w).

14. The low salt ophthalmic pharmaceutical composition according to claim 1, further comprising a pH adjustment agent.

15. The low salt ophthalmic pharmaceutical composition according to claim 14, wherein said pH adjustment agent is NaOH.

16. The low salt ophthalmic pharmaceutical composition according to claim 14 having pH about 7.3.

17. A low salt ophthalmic pharmaceutical composition comprising:
   a therapeutic lipid consisting essentially of castor oil at a concentration of about 0.25% (w/w);
   polysorbate 80 at a concentration of about 0.5% (w/w);
   acrylate/$C_{10}$-$C_{30}$ acrylate crosspolymer at a concentration of about 0.1% (w/w), wherein said acrylate/$C_{10}$-$C_{30}$ acrylate crosspolymer has a standard emulsion viscosity between 1,700 and 4,500 cPs;
   carboxymethylcellulose sodium at a concentration of about 0.5% (w/w);
   glycerin at a concentration of about 1.0% (w/w);
   a stabilized oxychloro complex preservative at a concentration of about 0.01% (w/w);
   boric acid at a concentration of about 0.6% (w/w);
   erythritol at a concentration of about 0.25% (w/w);
   levocarnitine at a concentration of about 0.25% (w/w);
   NaOH; and
   water.

18. A method for treating dry eye syndrome comprising:
   administering to a subject in need of treatment of dry eye syndrome a low salt ophthalmic pharmaceutical composition according to claim 1;
   thereby treating said dry eye syndrome.

* * * * *